United States Patent
Park et al.

(10) Patent No.: US 9,492,379 B2
(45) Date of Patent: *Nov. 15, 2016

(54) QUICKLY SOLUBLE ORAL FILM DOSAGE CONTAINING STEVIOSIDES AS A UNPLEASANT TASTE MASKING AGENT

(75) Inventors: Jin-Kyu Park, Gyeonggi-do (KR); Won-Suk Yang, Gyeonggi-do (KR); Kyoung Tae Jung, Seoul (KR)

(73) Assignee: CHABIO & DIOSTECH CO., LTD., Gyeonggi-do (KR)

( * ) Notice: Subject to any disclaimer, the term of this patent is extended or adjusted under 35 U.S.C. 154(b) by 101 days.

This patent is subject to a terminal disclaimer.

(21) Appl. No.: 13/572,336

(22) Filed: Aug. 10, 2012

(65) Prior Publication Data

US 2013/0039932 A1 Feb. 14, 2013

Related U.S. Application Data

(63) Continuation of application No. 13/260,959, filed as application No. PCT/KR2010/004020 on Jun. 22, 2010.

(30) Foreign Application Priority Data

Jun. 25, 2009 (KR) .................. 10-2009-0057276
Jun. 17, 2010 (KR) .................. 10-2010-0057450

(51) Int. Cl.
  *A61K 9/00* (2006.01)
  *A61K 9/70* (2006.01)
  *A61K 31/09* (2006.01)
  *A61K 31/14* (2006.01)
  *A61K 47/36* (2006.01)

(52) U.S. Cl.
  CPC .......... *A61K 9/0056* (2013.01); *A61K 9/006* (2013.01); *A61K 9/7007* (2013.01); *A61K 31/09* (2013.01); *A61K 31/14* (2013.01); *A61K 47/36* (2013.01)

(58) Field of Classification Search
  None
  See application file for complete search history.

(56) References Cited

U.S. PATENT DOCUMENTS

2004/0247649 A1* 12/2004 Pearce ............... A23G 3/36 424/440
2005/0147653 A1* 7/2005 Yasuda et al. ........... 424/443
2006/0204559 A1 9/2006 Bess et al.

(Continued)

FOREIGN PATENT DOCUMENTS

KR 10-2000-0001698 A 1/2000
KR 10-2004-0100483 A 12/2004

(Continued)

OTHER PUBLICATIONS

The Merck Index, O'Neil, Maryadele J et al., ed. 2006, 2012, entry for sildenafil.*

(Continued)

*Primary Examiner* — Sue Liu
*Assistant Examiner* — Thor Nielsen
(74) *Attorney, Agent, or Firm* — Kramer Amado P.C.

(57) ABSTRACT

Disclosed is a quickly soluble oral film dosage for masking a nasty taste, in particular, a quickly soluble oral film dosage comprising a stevioside based sweetener and a high potency sweetener in a ratio by weight (w/w) of 1:3 to 3:1, which may efficiently mask a bitter or nasty taste of a medicine and may be quickly dissolved in a mouth without water, thereby improving an aftertaste thereof thus enhancing dosage acceptability of a patient.

27 Claims, 5 Drawing Sheets

(56) References Cited

U.S. PATENT DOCUMENTS

| | | | |
|---|---|---|---|
| 2007/0116839 A1* | 5/2007 | Prakash et al. | 426/548 |
| 2009/0004254 A1 | 1/2009 | Maibach | |
| 2010/0240724 A1* | 9/2010 | Chang et al. | 514/394 |
| 2010/0285201 A1* | 11/2010 | Catani et al. | 426/594 |

FOREIGN PATENT DOCUMENTS

| | | |
|---|---|---|
| KR | 10-2005-0048056 A | 5/2005 |
| KR | 10-2009-0034729 A | 4/2009 |
| WO | WO 2008049256 A1 * | 5/2008 |

OTHER PUBLICATIONS

The Merck Index, O'Neil, Maryadele J et al., ed. 2006, 2012, entry for ondansetron.*

Schiffman et al., Brain Res Bull 38: 105-120 (1995).*

The Merck Index—montelukast 2006.*

Kinghorn et al., Medicinal Research Reviews 9: 91-115 (1989).*

International Search Report for corresponding PCT/KR2010/004020 (2 pages).

Schiffman et al., Synergism among Ternary Mixtures of Fourteen Sweeteners. Chem. Senses 25: 131-140, 2000.

Steviol Glycosides, Safety evaluation of certain food additives / prepared by the sixty-third meeting of the Joint FAO/ WHO Expert Committee on Food Additives (JEFCA). (WHO food additives series ; 54) WHO 2006, pp. 117-144. Viewed online at <http://whqlibdoc.who.int/publications/2006/9241660546_eng.pdf> on Apr. 11, 2013.

Lawless, "Theoretical Note: Tests of Synergy in Sweetener Mixtures," Chem. Senses 23: 447-351 (1998).

* cited by examiner

QUICKLY SOLUBLE ORAL FILM DOSAGE CONTAINING STEVIOSIDES AS A UNPLEASANT TASTE MASKING AGENT

This application is a continuation of U.S. application Ser. No. 13/260,959, filed on Sep. 29, 2011, as a U.S. National Stage application of PCT Application No. PCT/KR10/04020, filed on Jun. 22, 2010, the entire disclosures of which are hereby incorporated herein by reference.

This application claims priority to Korean Patent Application No. 10-2009-0057276, filed on Jun. 25, 2009 and Korean Patent No. 10-2010-0057450, filed on Jun. 17, 2010, in the Korean Intellectual Property Office, the entire contents of which are hereby incorporated by reference.

BACKGROUND OF THE INVENTION

1. Field of the Invention

The present invention relates to a quickly soluble oral film dosage for effectively masking a unpleasant taste and, more particularly, to a quickly soluble oral film dosage comprising a stevioside based sweetener and a high potency sweetener in a ratio by weight (w/w) of 1:3 to 3:1, which may efficiently mask a bitter or nasty taste of a medicine and may be quickly dissolved in a mouth without water, thereby improving an aftertaste thereof thus enhancing dosage acceptability of a patient.

2. Description of the Related Art

A social distribution ratio of aged population has currently increased owing to an extended span of human life Old people generally show degenerated abilities including eyesight, hearing, memory, physical strength, etc. as well as pharmacokinetic variation, thus requiring suitable medical therapy. Especially, since they have difficulties in swallowing typical tablets or capsules, an alternative oral dosage formulation for aged persons may be required.

A quickly soluble film easily disintegrated or dissolved in a mouth can be taken without water, thus being useful for aged persons who have difficulties in swallowing tablets or capsules, handicapped children, patients in bed, and the modern people living a busy life, and so forth. For aged persons and children, a liquid type formulation may be prescribed instead of tablets and/or capsules. However, such liquid formulation has disadvantages such as deteriorated stability and incorrect dosage.

In particular, when a drug is absorbed in an oral mucosa, it may avoid passage of the drug through the liver. Therefore, the quickly soluble film dosage is preferably used for some medicines subjected to liver metabolism.

However, a film formulation easily dissolved in an oral cavity enables a drug to be absorbed in the oral mucosa, causing a bitter or nasty taste of the drug during absorption. Accordingly, ideas for blocking or masking such bad taste may be required.

In view of the foregoing circumstances, International Patent Publication No. WO 2001/70194 describes preparation of a quickly soluble oral film dosage as a taste masking agent by adsorbing active ingredients to an ion-exchange resin. However, the ion-exchange resin contained in a water-soluble polymer may cause scratches during forming and require a complicated processing.

International Patent Publication No. WO 2003/070227 describes use of a chemical compound such as sodium hydrocarbonate generating carbon dioxide so as to mask taste. However, sodium hydrocarbonate has limitations in masking a strong bitter taste.

International Patent Publication No. WO 2008/040534 describes a film formulation disintegrated and entered into the stomach without adhesion to the oral mucosa. However, the foregoing film formulation is prepared by a complicated method for considerably preventing absorption of the formulation to the oral mucosa and may not provide beneficial effects for protection of the stomach and bowels.

U.S. Patent Laid-Open No. US 2008/0044454 describes a preparation method of a uniform film comprising coating of an active material by a variety of coating techniques then introducing the coated active material into a film forming agent. Such coating process may complicate the preparation of film.

SUMMARY OF THE INVENTION

The present inventors have made efforts to overcome the foregoing shortcomings and found that use of at least one selected from a group consisting of aspartame, acesulfame potassium, sucralose and neotame together with stevioside and/or its derivative can mask a bitter and/or nasty taste even without substantially altering a process of preparing an oral film dosage.

In other words, in order to solve conventional problems and to develop an improved quickly soluble oral film dosage containing active ingredients as the most preferable formulation, a great deal of studies and investigation have been conducted by the present inventors. As a result, they found that the bitter and/or nasty taste may be efficiently masked without additional coating processes if stevioside and/or derivatives thereof having a strong sweet aftertaste among high potency sweeteners are used together with any typical high potency sweetener, and then, completed the present invention.

Accordingly, it is an object of the present invention to provide a quickly soluble oral film dosage including a therapeutically effective amount of active pharmaceutical ingredient, stevioside and/or its derivative, at least one high potency sweetener, a film forming agent, and at least one of pharmaceutically available additives.

Another object of the present invention is to provide a quickly soluble oral film dosage capable of efficiently masking a nasty taste caused by a therapeutically effective amount of active pharmaceutical ingredient and, in addition, being promptly dissolved in an oral cavity.

In order to achieve the above objects, the present invention provides a quickly soluble oral film dosage, comprising: at least one water-soluble polymer; at least one active pharmaceutical ingredient; a stevioside based sweetener as an aftertaste enhancer; and at least one high potency sweetener (a primary sweetening agent) as a taste masking agent.

The proposed oral film dosage has excellent effects of masking a nasty taste and may be easily prepared by a simple process at low cost, thereby being preferably used in various applications such as an oral cleanser, a bad breath remover, a carrier for a nutrient supplementary agent, and a tongue soluble formulation enabling absorption of drugs in the oral cavity as well as the stomach and bowels, and so forth.

BRIEF DESCRIPTION OF THE DRAWINGS

These and other objects, features, aspects, and advantages of the present invention will be more fully described in the following detailed description of examples, taken in conjunction with the accompanying drawings. In the drawings.

Figure 3:
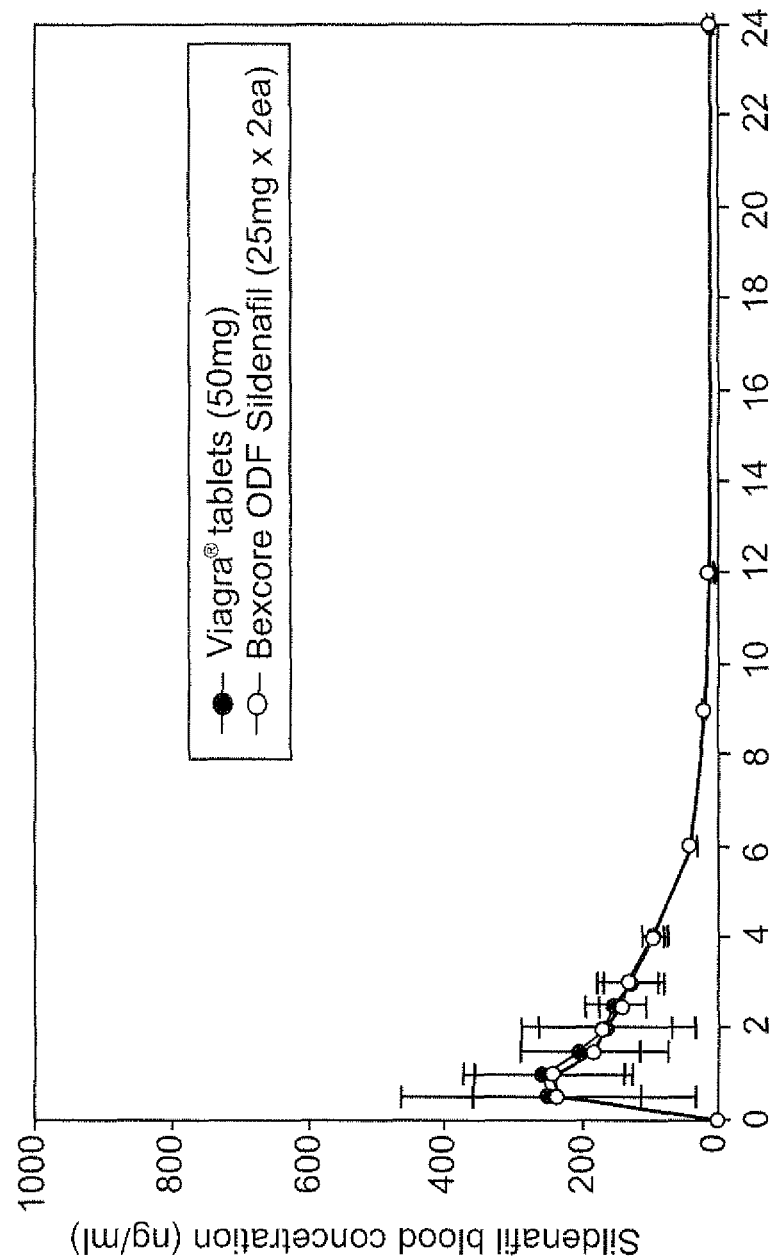
Figure 4:
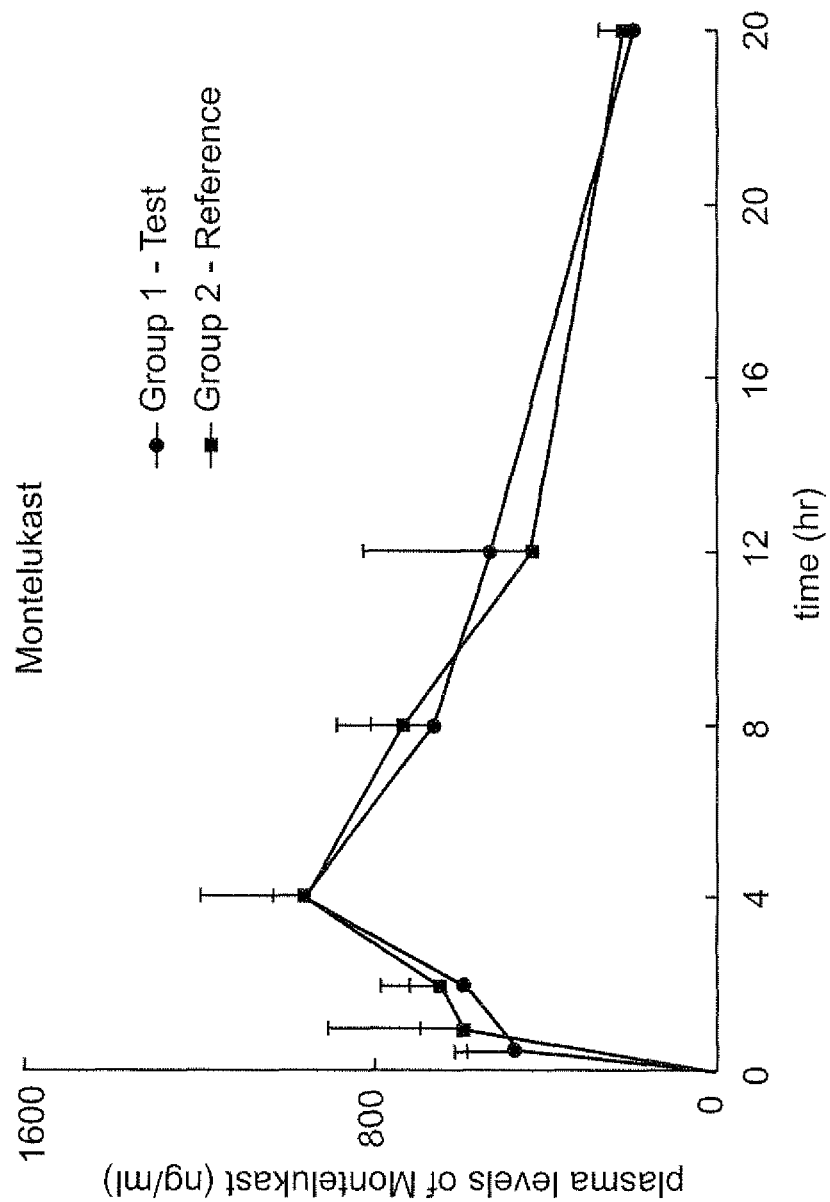
Figure 5:
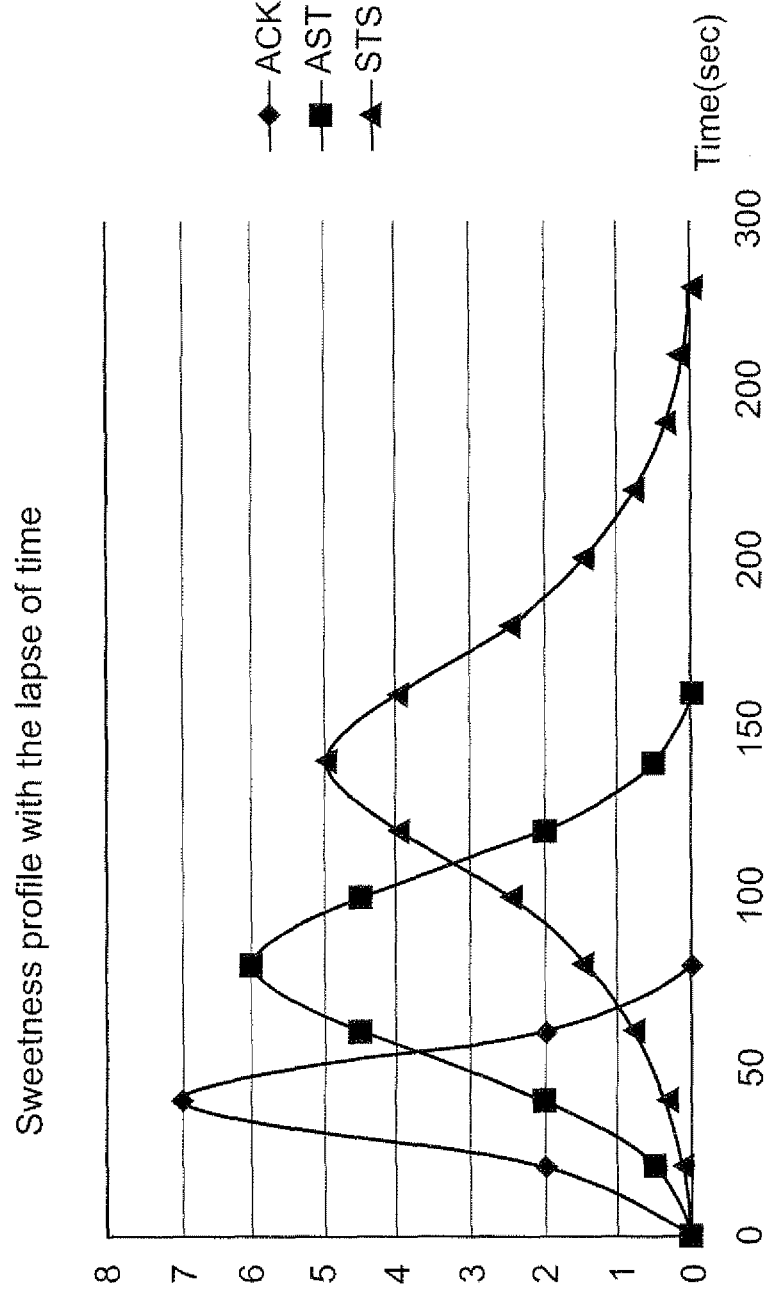

2 is a graph showing blood concentration profiles for pharmacokinetic tests using Ondansetron film dosage (8 mg) and Zofran® Zydis tablet (8 mg);

FIG. 3 is a graph showing blood concentration profiles for pharmacokinetic tests in comparison of Sildenafil Citrate film dosage (25 mg) and Viagra® tablet (25 mg);

FIG. 4 is a graph showing blood concentration profiles for oral administration tests to Beagle dogs using montelukast sodium film dosage (5 mg) and Singulair® chewable tablet (5 mg); and FIG. 5 is a graph showing sweetness profiles of high potency sweeteners (primary sweetening agents) according to an exemplary embodiment of the present invention; as shown in FIG. 5, acesulfame potassium (ACK), aspartame (AST) and stevioside (STS) exhibit delayed expression of sweetness in sequential order.

DETAILED DESCRIPTION OF THE INVENTION

The present invention describes a composition for a quickly soluble oral film dosage comprising active pharmaceutical ingredients, capable of efficiently masking a nasty taste as well as being rapidly dissolved in an oral cavity.

A preferred film dosage according to the present invention may include a active pharmaceutical ingredients, stevioside and/or its derivative, at least one high potency sweetener (a primary sweetening agent), a film forming agent, and at least one additional component described below.

Examples of the additional component may include pharmaceutically available additives such as a salivation stimulator, a thickener, a filler, a plasticizer, a secondary sweetening agent, an acidic agent, a flavor, an emulsifier, a surfactant, a binder, a preservative, a pigment, a coolant, and the like. Components of such additives will be described in great detail.

In the present invention, a quickly soluble film is obtained by dissolving a drug with a nasty taste, a high potency sweetener (a primary sweetening agent), stevioside and/or its derivative for improving an aftertaste in water or oil, emulsifying the solution, adding a water-soluble polymer and other additives to the emulsified solution, and forming the mixture into a shaped film.

As described above, the quickly soluble film of the present invention contains the primary sweetening agent with high potency sweetness, that is, the high potency sweetener.

According to an exemplary embodiment, the high potency sweetener (the primary sweetening agent) may include at least one sweetener selected from a group consisting aspartame, acesulfame salts, sucralose, saccharine salts, neotame, cyclamate salts, thaumatin, Luo han guo extract and licorice extract. The high potency sweetener more preferably includes at least one selected from a group consisting of aspartame, sucralose, neotame and acesulfame salts.

In case of chemicals with a strong nasty taste, they have a strong bitter taste and nasty taste in an aftertaste thereof. Adding 0.1 to 10 wt. % of stevioside based sweetener, that is, stevioside and/or its derivative relative to the total weight of the chemicals may mask the bitter and/or nasty taste.

Examples of stevioside may include Steviten Light (containing at least 98% of stevioside), Steviten Rich (containing 100% of enzyme treated stevia), Stevia extract REB-A 73% (containing at least 73% of Rebaudioside A), and Rebaten 97% (containing at least 97% of Rebaudioside A) etc., all of which are manufactured by DaePyung Co. Ltd. in Korea.

Among these, the enzyme treated stevia is a product with improved taste prepared using sugar transferase in order to add glucose to the stevia extract, thus reducing an inherent bitter taste of stevioside while increasing solubility thereof. The stevia extract Rebaten 97% shows the highest sweetness and the most excellent equality sweetness among seven (7) kinds of sweet ingredients contained in stevia and is obtained from stevia by an alternative separation process.

As for maximum sweetness of each of high potency sweeteners after the lapse of time shown in FIG. 5, acesulfame potassium (ACK) firstly expresses the maximum sweetness, followed by aspartame, sucralose and stevioside in sequential order. Therefore, a nasty taste remained after a drug is absorbed in an oral cavity may be controlled by stevioside most slowly expressing sweetness.

The quickly soluble oral film dosage of the present invention may include a water-soluble polymer.

Examples of the water-soluble polymer may include pullulan, gelatin, pectin, low viscosity pectin, hydroxypropylmethyl cellulose, low viscosity hydroxylpropylmethyl cellulose, hydroxyethyl cellulose, hydroxypropyl cellulose, carboxymethyl cellulose, polyvinylalcohol, polyacrylic acid, methyl methacrylate copolymer, carboxyvinyl polymer, polyethyleneglycol, alginic acid, low viscosity alginic acid, sodium alginate, modified starch, casein, whey protein extract, soy protein extract, zein, levan, elsinan, gluten, acacia gum, carageenan, Arabic gum, guar gum, locust bean gum, xanthan gum, gellan gum, agar, and the like.

Preferably, the water-soluble polymer may include at least one selected from a group consisting of pullulan, gelatin, pectin, low viscosity pectin, low viscosity alginic acid, hydroxypropylmethyl cellulose, and modified starch.

An amount of such water-soluble polymer in the quickly soluble film may range from 50 to 90 wt. %, preferably 60 to 80 wt. %, and more preferably 60 to 70 wt. % relative to the total weight of the quickly soluble film.

The active pharmaceutical ingredient used in the quickly soluble film may be any of pharmacologically active substances for oral administration, in particular, be capable of being quickly dissolved to rapidly express efficacy of a medicine. Examples of such substances may include: diabetic remedy such as glimepiride, pioglitazone, etc.; insomnia remedy such as zolpidem, eszopiclone, etc.; genitorurinary remedy such as tolterodine, trospium, etc.; obesity remedy such as sibutramine; enzyme formulation such as streptokinase; gastric ulcer remedy such as omeprazole; cough remedy and expectorant such as theophylline, clenbuterol, etc.; dermal disorder remedy such as finasteride; antiemitic drug such as ondansetron; antidepression drug such as fluoxetine; antihistamine drug such as fexofenadine hydrochloride; antipyretic, analgesic and antiphlogistic remedy such as aspirin, ibuprofen, ketoprofen, meloxicam, etc.; hormone drug such as testosterone; circulatory organ remedy such as felodipine, atorvastatin, amlodipine camsylate, doxazosin, simvastatin, lercanidipine, etc.; gastrointestinal remedy such as famotidine, ranitidine, lansoprazole, etc.; heart vascular disease remedy such as amlodipine, nitroglycerin, etc.; psychoneurotic drug such as paroxetine; impotency remedy such as sildenafil, tadalafil, vardenafil, etc.; Alzheimer's disease remedy such as donepezil; osteoporosis remedy; arthritis remedy; epilepsy remedy; muscle relaxing agent; cerebral function enhancer; schizophrenia remedy; immuno-suppression agent; antibiotic agent such as ampicillin, amoxicillin; anticancer agent; Supportives in tumor therapy; vaccine; oral cleanser; anemia remedy; constipation remedy; allergy remedy; anti-blood coagulation agent; oral vaccine; melatonin; vitamin; nutrient; probiotic preparation, multi-symptom cold/flue medications; health functional foods, and so forth.

The active pharmaceutical ingredient may be at least one selected from a group consisting of triclosan, cetylpyridium chloride, domiphen bromide, quaternary ammonium salt, zinc compounds, sanguinarine, fluoride, alexidine, octenidine, EDTA, aspirin, acetaminophen, ibuprofen, ketoprofen, diflunisal, fenoprofen calcium, naproxen, tolmetin sodium, indomethacin, benzonatate, caramiphen, edisylate, menthol, dextromethorphan hydrobromide, chlophedianol hydrochloride, diphenhydramine, pseudoephedrine hydrochloride, phenylephrine, phenylpropanolamine, pseudoephedrine sulfate, bromophenylamine maleate, chlorophenylamine maleate, carbinoxamine maleate, clemastine fumarate, dexchlorpheniramine maleate, diphenhydramine hydrochloride, diphenhydramine citrate, diphenylpyraline hydrochloride, doxylamine succinate, promethazine hydrochloride, pyrilamine maleate, tripelennamine citrate, triprolidine hydrochloride, acrivastine, loratadine, brompheniramine, dexbrompheniramine, guaifenesin, ipecac, calcium iodide, terpine hydrate, loperamide, famotidine, ranitidine, omeprazole, lansoprazole, aliphatic alcohol, nicotine, caffeine, strychnine, picrotoxin, pentylenetetrazol, phenylhydantoin, phenobarbital, primidone, carbamazepine, ethosuximide, methosuximide, phensuximide, trimethadione, diazepam, benzodiazepine, phenacemide, pheneturide, acetazolamide, sulthiame, bromide, levodopa, amantadine, morphine, heroin, hydromorphone, methophone, oxymorphone, levorphanol, codeine, hydrocodone, xycodone, nalorphine, naloxone, naltrexone, salicylate, phenylbutazone, indomethacin, phenacetin, chloropromazine, methotrimeprazine, haloperidol, clozapine, reserpine, imipramine, tranylcypromine, phenelzine, lithium, apomorphine, sildenafil, tadalafil, vardenafil, ondansetron, donepezil, zolpidem tartrate, granisetron, montelukast, pholcodine, butylscopolamine, fentanyl citrate, oxycodone hydrochloride, buprenorphine hydrochloride, escitalopram oxalate, rivastigmine tartrate, esomeprazole magnesium, aripiprazole, zolmitriptan, rizatriptan benzoate, telmisartan, risperidone, benzocaine, cetirizine hydrochloride, bambuterol hydrochloride, galantamine hydrobromide, lercanidipine hydrochloride, paroxetine hydrochloride, meloxicam, tolterodine tartrate, doxazosin mesylate, and pharmaceutically available salts thereof.

If one of the ondansetron salts is an ondansetron hydrochloride, a quickly soluble film including the ondansetron hydrochloride as the active pharmaceutical ingredient may have bioequivalence.

If one of the montelukast salts is a montelukast sodium, a quickly soluble film including the montelukast sodium as the active pharmaceutical ingredient may have bioequivalence.

If one of the sildenafil salts is a sildenafil citrate, a quickly soluble film including the sildenafil citrate as the active pharmaceutical ingredient may have bioequivalence.

An amount of such active ingredient may range from 0.1 to 30 wt. %, preferably 10 to 20 wt. % relative to the total weight of the quickly soluble film.

The filler may reduce greasy features of the film in the mouth and endow a skeleton structure to the film. In addition, adhesion between films is decreased while a film disintegration speed and a drug elution rate as well as stickiness may be controlled. An amount of the filler may range from 1 to 15 wt. % relative to the total weight of the quickly soluble film.

As for an exemplary embodiment, the filler may include at least one selected from a group consisting of microcrystalline cellulose, cellulose polymer, magnesium carbonate, calcium carbonate, limestone powder, silicate, clay, talc, titanium dioxide and calcium phosphate.

A plasticizer may be used to regulate flexibility of the film. An amount of the plasticizer in the quickly soluble film may range from 0.1 to 15 wt. % relative to the total weight of the quickly soluble film.

As for an exemplary embodiment, the plasticizer may be at least one selected from a group consisting of sorbitol, maltitol, xylitol, glycerin, polyethyleneglycol, propyleneglycol, hydrogenated starch syrup, starch syrup, triacetin, glycerol oleate, sucrose fatty acid ester and double chain fatty acid.

The quickly soluble film of the present invention may further include a secondary sweetening agent in an amount of 0.1 to 10 wt. % relative to the total weight of the quickly soluble film.

As for an exemplary embodiment, the secondary sweetening agent may be at least one selected from a group consisting of sucrose, glucose, maltose, oligosaccharides dextrin, alpha cyclodextrin, beta cyclodextrin, gamma cyclodextrin, methyle beta cyclodextrin, hydroxypropy beta cyclodextrin, cluster dextrin, indigestible dextrin, hydrogenated indigestible dextrin, invert sugar, fructose, lactose, galactose, starch syrup, sorbitol, maltitol, xylitol, erythritol, hydrogenated starch syrup, mannitol and trehalose.

The quickly soluble film of the present invention may further include an acidic agent. The acidic agent serves to control taste together with the sweetener and may function to stimulate secretion of saliva in order to dissolve the quickly soluble film. An amount of the acidic agent may range from 0.1 to 10 wt. % relative to the total weight of the quickly soluble film.

As for an exemplary embodiment, the acidic agent may be at least one selected from a group consisting of citric acid, malic acid, fumaric acid, tartaric acid, ascorbic acid, succinic acid, adipic acid and lactic acid.

The quickly soluble oral film dosage of the present invention may further include flavor. The inventive film dissolved and absorbed in an oral cavity may need appropriate flavor. Such flavor may natural flavor, artificial flavor or a mixture thereof.

The natural flavor may include aromatic plants, especially, extract and/or oil obtained from leaves, flowers, fruits of the aromatic plants. The plant oil may include spearmint oil, cinnamon oil, peppermint oil, lemon oil, clove oil, bay oil, thyme oil, cedar leaf oil, nutmeg oil, sage oil, almond oil, and the like. The artificial flavor may include synthetic fruit flavors such as lemon, orange, grape, lime, strawberry, etc. and other synthetic flavors such as vanilla, chocolate, coffee, cocoa, pine leaf, ginseng, red ginseng, citrus, etc.

An amount of such flavor depends on various parameters such as types, kinds and/or desired levels of the flavors commonly used in the art and, may range from 1 to 15 wt. % relative to the total weight of the quickly soluble film.

When the oil type flavor is used, an emulsifier may be added in order to enable the flavor to be miscible with water-soluble substances. An amount of the emulsifier depends on kind or amount of the flavor and may range from 0.1 to 10 wt. % relative to the total weight of the quickly soluble film.

As for an exemplary embodiment, the emulsifier may be at least one selected from a group consisting of glycerin fatty acid ester, sucrose fatty acid ester, lecithin, enzyme treated lecithin, polysorbate, sorbitan fatty acid ester and propyleneglycol.

The quickly soluble oral film dosage of the present invention may further include an appropriate pigment. An amount of the pigment is varied as needed and may range from 0.01 to 10 wt. % relative to the total weight of the quickly soluble film. The pigment may include natural and/or synthetic pigment.

The quickly soluble oral film dosage may further include a cooling agent. The cooling agent is not particularly limited but includes, for example, WS3, WS23 or questice-L. An amount of the cooling agent is varied as needed and may range from 0.01 to 5 wt. % relative to the total weight of the quickly soluble film.

The present invention provides a quickly soluble film comprising a quickly soluble oral film dosage composition.

The inventive film is preferably a thin film to maintain desired tensile strength and other physical strength even in the form of very thin film. As for an exemplary embodiment, the quickly soluble film may have a thickness of 20 μm to 200 μm and, preferably, 40 μm to 100 μm.

The present invention provides a method for preparation of a quickly soluble oral film dosage.

As an exemplary embodiment of the present invention, the method for preparation of a quickly soluble film includes:

(1) preparing a quickly soluble film composition comprising an active ingredient, at least two high potency sweeteners and a water-soluble polymer;

(2) introducing the prepared film composition into a molding machine to form a film at 50 to 80□; and (3) ageing the formed film for 1 to 10 days under 50 to 70% relative humidity.

The method for preparation of the quickly soluble oral film dosage according to the present invention may be performed by the following processes.

(1) Solution Preparing Process a) Preparation of first solution: The water-soluble polymer is placed in boiling water to be completely dissolved.

b) Preparation of second solution: Additives such as a pigment, a sweetener, an acidic agent and/or a filler are combined together to prepare the second solution.

c) Preparation of third solution: All of an active ingredient, menthol, a flavor and a cooling agent are mixed with an emulsifier to prepare the third solution.

d) Preparation of fourth solution: Blending the second and third solutions results in the fourth solution.

e) Preparation of fifth solution: After raising the temperature to 60□ or more, the fourth solution is combined with the first solution to prepare the fifth solution.

(2) Forming Process

After filtering the fifth solution, the filtered solution is introduced into a molding machine to form a film. The temperature of the molding machine ranges from 50 to 80□ and produces the film in a roll form via a belt drum drier.

(3) Ageing Process

The formed film is subjected to an ageing process for 1 to 10 days under 50 to 70% relative humidity, so as to have a water content suitable for slitting or cutting. Such water content may range from 8 to 12%.

In addition, the following processes may be further performed after the above processes.

(4) Cutting Process

After slitting the aged roll of film in to smaller rolls, the smaller rolls are cut into desired sizes followed by putting them in containers and/or aluminum foils.

(5) Packaging Process

The containers and/or aluminum foils having the products are packaged into small boxes or manufactured into final products through blistering.

According to the foregoing preparation method, the present invention may provide the quickly soluble film without a nasty taste only by adding stevioside and/or its derivative, regardless of applying specific techniques to coat active ingredients contained in the film.

Also, the quickly soluble film prepared according to the present invention may be rapidly disintegrated and dissolved by saliva in a mouth without requiring water, so as to be easily administrated to a patient, aged person and/or child who have difficulties in swallowing typical tablets.

Hereinafter, the present invention will be described in greater detail by the following examples. However, these examples are intended for illustrative purposes and a person skilled in the art will appreciate that the present invention is not restricted thereto.

EXAMPLES

Examples 1 to 3 and Comparative Examples 1 to 3

Meloxicam as an active pharmaceutical ingredient was added to prepare films having constitutional compositions shown in the following Table 1. Six (6) adult men and women orally took the prepared films. A time period spent for completely dissolving the film with saliva in an oral cavity was measured and a sensory test was performed. The sensory test was randomly conducted and test results are show in the following Table 2.

TABLE 1

| Ingredient | Comparative example 1 (wt. %) | Comparative example 2 (wt. %) | Comparative example 3 (wt. %) | Example 1 (wt. %) | Example 2 (wt. %) | Example 3 (wt. %) |
|---|---|---|---|---|---|---|
| Aspartame | 2.5 | | | 2.5 | | |
| Sucralose | | 2.5 | | | 2.5 | |
| Acesulfame potassium | | | 2.5 | | | 2.5 |
| Stevitenrich | | | | 3.5 | | |
| Enzyme treated stevia | | | | | 3.5 | |
| Rebaten 97% | | | | | | 3.5 |

TABLE 1-continued

| Ingredient | Comparative example 1 (wt. %) | Comparative example 2 (wt. %) | Comparative example 3 (wt. %) | Example 1 (wt. %) | Example 2 (wt. %) | Example 3 (wt. %) |
|---|---|---|---|---|---|---|
| Citric acid | 0.6 | 0.6 | 0.6 | 0.6 | 0.6 | 0.6 |
| Oxidated starch | 5 | 5 | 5 | 5 | 5 | 5 |
| Lecithin | 0.4 | 0.4 | 0.4 | 0.4 | 0.4 | 0.4 |
| Menthol | 0.5 | 0.5 | 0.5 | 0.5 | 0.5 | 0.5 |
| Carageenan | 0.2 | 0.2 | 0.2 | 0.2 | 0.2 | 0.2 |
| Polysorbate 80 | 0.4 | 0.4 | 0.4 | 0.4 | 0.4 | 0.4 |
| Peppermint oil | 0.8 | 0.8 | 0.8 | 0.8 | 0.8 | 0.8 |
| Pullulan | 66.6 | 66.6 | 66.6 | 63.1 | 63.1 | 63.1 |
| Microcrystalline cellulose | 3 | 3 | 3 | 3 | 3 | 3 |
| Lemon flavor | 2 | 2 | 2 | 2 | 2 | 2 |
| Meloxicam | 18 | 18 | 18 | 18 | 18 | 18 |
| Total weight | 100.0 | 100.0 | 100.0 | 100.0 | 100.0 | 100.0 |

*an input amount of each component was calculated under the presumption that a water content of the prepared film is 10%.

As a result of the foregoing sensory test, it was found that the compositions not containing stevioside and/or its derivative (Comparative Example 1, 2 and 3) and the compositions containing the same (Examples 1, 2 and 3) showed no substantial difference in terms of disintegration time in the mouth. However, the compositions containing stevioside had superior effects of masking a nasty taste over the compositions without stevioside. These results are shown in Table 2.

As for raw materials used, herein, aspartame and oxidated starch were manufactured by Daesang Co. Ltd., acesulfame potassium was manufactured by Nutrinova GmbH, sucralose was manufactured by Tate and Lyle plc, carageenan was manufactured by MSC, polysorbate was manufactured by Ilsin Wells, pululan was manufactured by Hayashibara Co. Ltd., and peppermint oil and lemon flavor were manufactured by Bolak Co. Ltd.

TABLE 2

Sensory test result

| | Sweetener | Disintegration time in mouth (sec) | Initial result of sensory test | sensory test result after 1 minute |
|---|---|---|---|---|
| Comparative example 1 | Aspartame | 55 | 1 | 5 |
| Comparative example 2 | Sucralose | 53 | 1 | 4 |
| Comparative example 3 | Acesulfame potassium | 54 | 1 | 5 |
| Example 1 | Aspartame + steviten-rich | 51 | 1 | 1 |
| Example 2 | Sucralose + enzyme treated stevioside | 52 | 1 | 1 |
| Example 3 | Acesulfame potassium + rebaten 97% | 53 | 1 | 1 |

* As the test result value increases, a nasty taste is strong.

Examples 4 to 8 and Comparative Examples 4 to 8

After altering kinds of the water-soluble polymers and using meloxicam as a active pharmaceutical ingredient films having constitutional compositions shown in the following Tables 3 and 4 were prepared. Six (6) adult men and women orally took the prepared films. A time period spent for completely dissolving the film with saliva in an oral cavity was measured and a sensory test was performed. The sensory test was randomly conducted and test results are show in the following Table 5.

TABLE 3

| Ingredient | Example 4 (wt. %) | Example 5 (wt. %) | Example 6 (wt. %) | Example 7 (wt. %) | Example 8 (wt. %) |
|---|---|---|---|---|---|
| Sucralose | 2.5 | 2.5 | 2.5 | 2.5 | 2.5 |
| Steviten-rich | 3.5 | 3.5 | 3.5 | 3.5 | 3.5 |
| Citric acid | 0.6 | 0.6 | 0.6 | 0.6 | 0.6 |
| Hydroxypropyl starch | 5 | 5 | 5 | 5 | 5 |
| Lecithin | 0.4 | 0.4 | 0.4 | 0.4 | 0.4 |
| Menthol | 0.5 | 0.5 | 0.5 | 0.5 | 0.5 |
| Carageenan | 0.2 | 0.2 | 0.2 | 0.2 | 0.2 |
| Polysorbate 80 | 0.4 | 0.4 | 0.4 | 0.4 | 0.4 |
| Peppermint oil | 0.8 | 0.8 | 0.8 | 0.8 | 0.8 |
| Low viscosity pectin | 63.1 | | | | |
| Gelatin | | 63.1 | | | |
| HPMC | | | 63.1 | | |
| Low viscosity alginic acid | | | | 63.1 | |
| Polyvinyl alcohol | | | | | 63.1 |
| Microcrystalline cellulose | 3 | 3 | 3 | 3 | 3 |
| Lemon flavor | 2 | 2 | 2 | 2 | 2 |
| Meloxicam | 18 | 18 | 18 | 18 | 18 |
| Total weight | 100.0 | 100.0 | 100.0 | 100.0 | 100.0 |

* An input amount of each component was calculated under the presumption that a water content of the prepared film is 10%.

TABLE 4

| Ingredient | Comparative Example 4 (wt. %) | Comparative Example 5 (wt. %) | Comparative Example 6 (wt. %) | Comparative Example 7 (wt. %) | Comparative Example 8 (wt. %) |
|---|---|---|---|---|---|
| Sucralose | 2.5 | 2.5 | 2.5 | 2.5 | 2.5 |
| Citric acid | 0.6 | 0.6 | 0.6 | 0.6 | 0.6 |
| Hydroxypropyl starch | 5 | 5 | 5 | 5 | 5 |

TABLE 4-continued

| Ingredient | Comparative Example 4 (wt. %) | Comparative Example 5 (wt. %) | Comparative Example 6 (wt. %) | Comparative Example 7 (wt. %) | Comparative Example 8 (wt. %) |
|---|---|---|---|---|---|
| Lecithin | 0.4 | 0.4 | 0.4 | 0.4 | 0.4 |
| Menthol | 0.5 | 0.5 | 0.5 | 0.5 | 0.5 |
| Carageenan | 0.2 | 0.2 | 0.2 | 0.2 | 0.2 |
| Polysorbate 80 | 0.4 | 0.4 | 0.4 | 0.4 | 0.4 |
| Peppermint oil | 0.8 | 0.8 | 0.8 | 0.8 | 0.8 |
| Low viscosity pectin | 66.6 | | | | |
| Gelatin | | 66.6 | | | |
| HPMC | | | 66.6 | | |
| Low viscosity alginic acid | | | | 66.6 | |
| Polyvinyl alcohol | | | | | 66.6 |
| Microcrystalline cellulose | 3 | 3 | 3 | 3 | 3 |
| Lemon flavor | 2 | 2 | 2 | 2 | 2 |
| Meloxicam | 18 | 18 | 18 | 18 | 18 |
| Total weight | 100.0 | 100.0 | 100.0 | 100.0 | 100.0 |

* An input amount of each component was calculated under the presumption that a water content of the prepared film is 10%.

As a result of the foregoing sensory test, it was found that the disintegration time in the mouth was substantially the same and the nasty taste masking effects were excellent, regardless of different kinds of water-soluble polymers. These results are shown in Table 5.

As raw materials used, herein, the low viscosity pectin was GENU pectin DSS manufactured by CP Kelco ApS, gelatin was 100 Bloom products manufactured by Geltech, hydroxypropylmethyl cellulose was Demacol HE 5/6 BV manufactured by Demasa, the low viscosity alginic acid was Login manufactured by MSC, and hydroxypropyl starch was products manufactured by Grain Processing Corp.

TABLE 5

| | Sweetener | Water soluble polymer | Disintegration time in mouth (sec) | Initial result of sensory test | Sensory test result after 1 minute |
|---|---|---|---|---|---|
| Example 4 | Sucralose + stevitenrich | Pectin | 57 | 1 | 1 |
| Comparative example 4 | Sucralose | Pectin | 59 | 1 | 4 |
| Example 5 | Sucralose + stevitenrich | Gelatin | 54 | 1 | 1 |
| Comparative example 5 | Sucralose | Gelatin | 55 | 1 | 4 |
| Example 6 | Sucralose + stevitenrich | HPMC | 53 | 1 | 1 |
| Comparative example 6 | Sucralose | HPMC | 54 | 1 | 4 |
| Example 7 | sucralose + stevitenrich | Alginic acid | 56 | 1 | 1 |
| Comparative example 7 | Sucralose | Alginic acid | 58 | 1 | 4 |
| Example 8 | Sucralose + stevitenrich | PVA | 53 | 1 | 1 |
| Comparative example 8 | Sucralose | PVA | 54 | 1 | 4 |

* As the test result value increases, a nasty taste is strong.

Examples 9 to 13 and Comparative Examples 9 to 13

As active pharmaceutical ingredients, ondansetron zolpidem tartrate, tadalafil, lercanidipine, and/or donepezil were added to prepare films having constitutional compositions shown in the following Table 6. Table 7 shows constitutional compositions without stevioside.

According to the constitutional compositions shown in Tables 6 and 7, the films were prepared. Six (6) adult men and women orally took the prepared films. A time period spent for completely dissolving the film with saliva in an oral cavity was measured and a sensory test was performed.

The sensory test was randomly conducted and test results are show in the following Table 8.

TABLE 6

| Ingredient | Example 9 (wt. %) | Example 10 (wt. %) | Example 11 (wt. %) | Example 12 (wt. %) | Example 13 (wt. %) |
|---|---|---|---|---|---|
| Sucralose | | | | 1 | 1.2 |
| Aspartame | 4 | 3 | 3 | 1 | 1.2 |
| Acesulfame potassium | | | 1 | | |
| Rebaten 97% | 4 | 3 | 2 | 1 | 1.2 |
| Citric acid | 0.2 | 0.2 | 0.2 | 0.6 | 0.6 |
| Hydroxypropyl starch | 4 | 4 | 2 | 0.3 | 4 |
| Lecithin | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Polysorbate 80 | 0.4 | 0.5 | 0.3 | 0.3 | 0.3 |
| Peppermint oil | 0.8 | 2.7 | 0.6 | 3 | 3 |
| Pullulan | 72.5 | 59.4 | 68.2 | 72.1 | 68.4 |
| Microcrystalline cellulose | 1.4 | 1.4 | 0.7 | 0.7 | 4 |
| Lemon flavor | 2 | 2 | 1.5 | 1.5 | 1.5 |
| Ondansetron | 10.1 | | | | |
| Zolpidem tartrate | | 20.9 | | | |
| Tadalafil | | | 20.0 | | |
| Lercanidipine | | | | 15 | |
| Donepezil | | | | | 10 |
| Total weight | 100.0 | 100.0 | 100.0 | 100.0 | 100.0 |

* An input amount of each component was calculated under the presumption that a water content of the prepared film is 10%.

TABLE 7

| Ingredient | Comparative Example 9 (wt. %) | Comparative Example 10 (wt. %) | Comparative Example 11 (wt. %) | Comparative Example 12 (wt. %) | Comparative Example 13 (wt. %) |
|---|---|---|---|---|---|
| Sucralose | | | | 1 | 1.2 |
| Aspartame | 4 | 3 | 3 | 1 | 1.2 |
| Acesulfame potassium | | | 1 | | |

TABLE 7-continued

| Ingredient | Comparative Example 9 (wt. %) | Comparative Example 10 (wt. %) | Comparative Example 11 (wt. %) | Comparative Example 12 (wt. %) | Comparative Example 13 (wt. %) |
|---|---|---|---|---|---|
| Rebaten 97% | 0 | 0 | 0 | 0 | 0 |
| Citric acid | 0.2 | 0.2 | 0.2 | 0.6 | 0.6 |
| Hydroxypropyl starch | 4 | 4 | 2 | 0.3 | 4 |
| Lecithin | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Polysorbate 80 | 0.4 | 0.5 | 0.3 | 0.3 | 0.3 |
| Peppermint oil | 0.8 | 2.7 | 0.6 | 3 | 3 |
| Pullulan | 76.5 | 62.4 | 70.2 | 73.1 | 70.6 |
| Microcrystalline cellulose | 1.4 | 1.4 | 0.7 | 0.7 | 4 |
| Lemon flavor | 2 | 2 | 1.5 | 1.5 | 1.5 |
| Ondansetron | 10.1 | | | | |
| Zolpidem tartrate | | 20.9 | | | |
| Tadalafil | | | 20.0 | | |
| Lercanidipine | | | | 15 | |
| Donepezil | | | | | 10 |
| Total weight | 100.0 | 100.0 | 100.0 | 100.0 | 100.0 |

* An input amount of each component was calculated under the presumption that a water content of the prepared film is 10%.

As a result of the foregoing sensory test, it was found that the disintegration time in the mouth was substantially the same regardless of different kinds of active ingredients while addition of stevioside exhibited excellent effects of masking an aftertaste which remained after 1 minute. These results are shown in Table 8.

TABLE 8

| | Sweetener | Disintegration time in mouth (sec) | Initial result of sensory test | Sensory test result after 1 minute |
|---|---|---|---|---|
| Example 9 | aspartame + Rebaten 97% | 53 | 1 | 1 |
| Comparative example 9 | Aspartame | 54 | 1 | 5 |
| Example 10 | Aspartame + Rebaten 97% | 49 | 1 | 1 |
| Comparative example 10 | Aspartame | 50 | 1 | 5 |
| Example 11 | Aspartame + acesulfame potassium + Rebaten 97% | 51 | 1 | 1 |
| Comparative example 11 | Aspartame + acesulfame potassium | 52 | 1 | 4 |
| Example 12 | Sucralose + aspartame + Rebaten 97% | 53 | 1 | 1 |
| Comparative example 12 | Sucralose + aspartame | 55 | 1 | 4 |
| Example 13 | Sucralose + aspartame + Rebaten 97% | 52 | 1 | 1 |
| Comparative example 13 | Sucralose + aspartame | 53 | 1 | 4 |

* As the test result value increases, a nasty taste is strong.

Example 14

Figure 1:
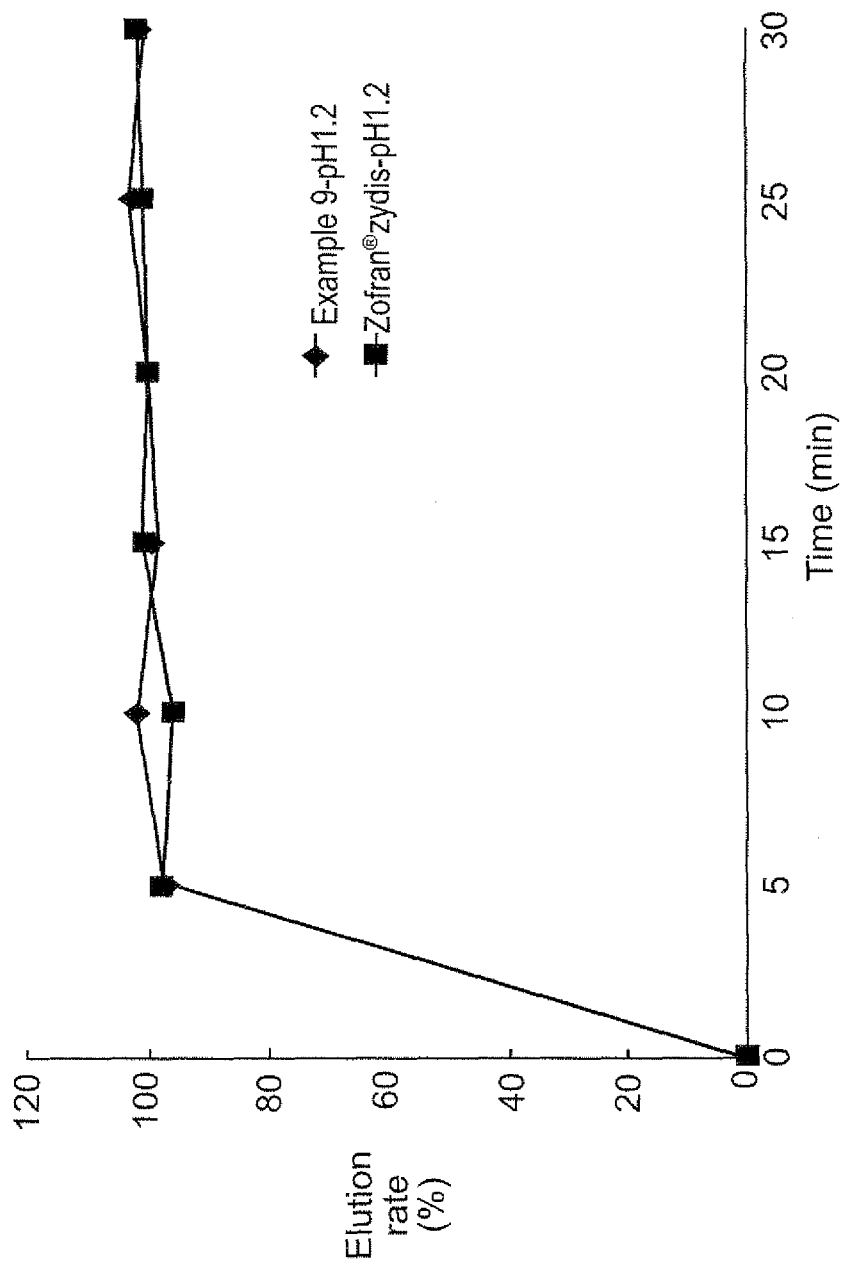
FIG. 1 is a graph showing results of dissolution experiments for a quickly soluble oral film dosage prepared at pH 1.2 according to Example 9 of the present invention in comparison with a control (Zofran® Zydis tablet available from GlaxoSmithKline Co., 8 mg)

Ondansetron based quickly soluble film prepared according to Example 9 of the present invention was subjected to dissolution experiments at pH 1.2 in comparison with a conventional product named Zofran® Zydis tablet containing ondansetron available from GlaxoSmithKline Co. (GSK) based on Notice of the Food and Drug Administration and the experimental results are shown in FIG. 1. As shown in the accompanying drawings, there was no substantial difference in elution between both of the formulations.

Example 15

Ondansetron based quickly soluble film prepared according to Example 9 of the present invention was subjected to pharmacokinetic tests in comparison with a conventional product named Zofran® Zydis tablet containing ondansetron available from GlaxoSmithKline Co. (GSK). The experiments is conducted for healthy fourteen (14) adult men and women with Latin square method based on Notice of bioequivalence test standard of the Food and Drug Administration.

Figure 2:
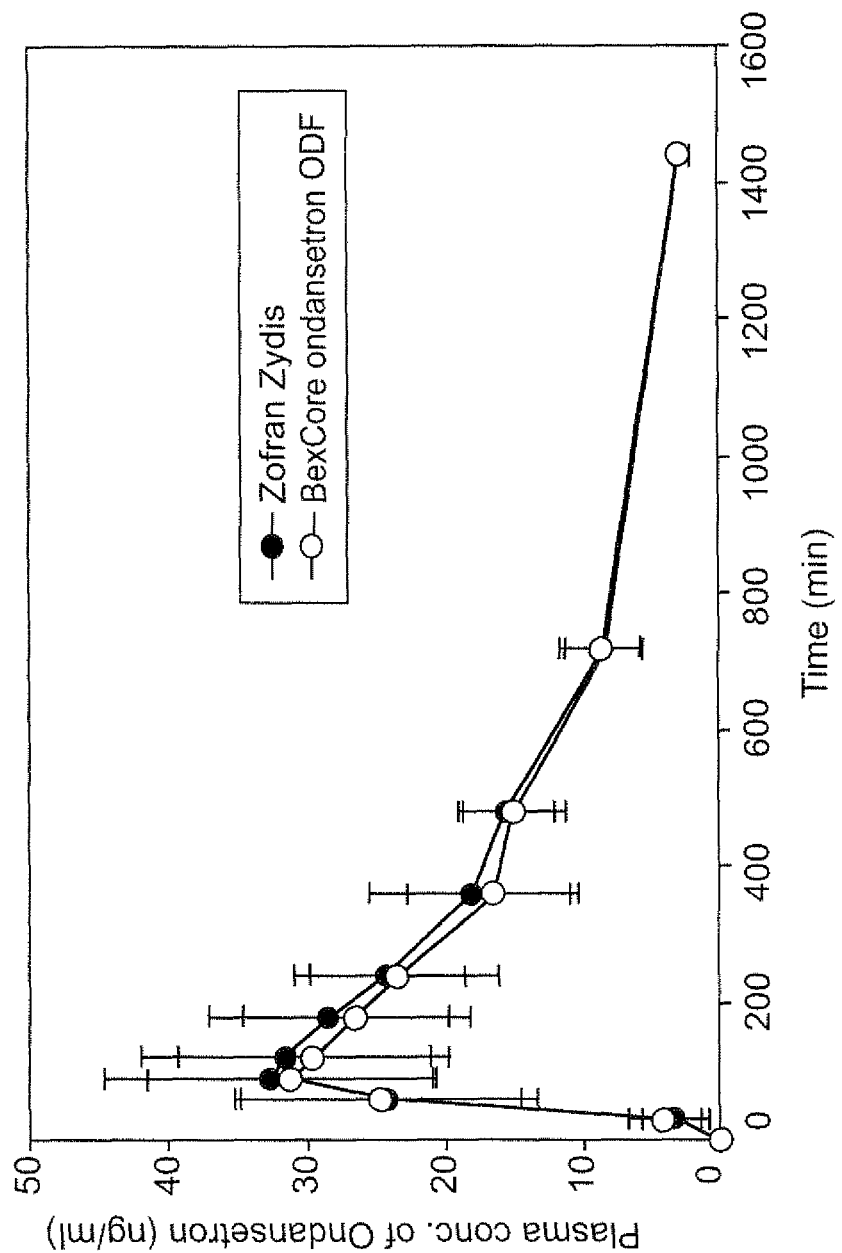

The experimental results are shown in Table 9 and FIG. 2. It was confirmed that the inventive film of this example has the bioequivalence as shown in Table 9 and FIG. 2.

TABLE 9

Pharmacokinetic test result of ondansetron film formulations

| Parameter | Group 1 | Group 2 |
|---|---|---|
| AUC0~24 (ng · hr/mL) | 244.78 ± 91.83 | 259.64 ± 87.10 |
| Cmax (ng/mL) | 30.93 ± 10.71 | 33.16 ± 8.89 |
| Tmax (hr) | 1.86 ± 0.71 | 1.94 ± 0.75 |

Note 1)
Group 1 is Ondansetron film formulations (8 mg).
Group 2 is Zorfran® Zydis ODTs Example 16 to 20

As active pharmaceutical ingredients, sildenafil free base, sildenafil lactate, sildenafil citrate, granisetron, and montelukast sodium were added to prepare films having constitutional compositions shown in the following Table 10. The sensory test was randomly conducted and test results were that unpleasant aftertaste was well masked.

TABLE 10

| Ingredient | Example 15 (wt. %) | Example 16 (wt. %) | Example 17 (wt. %) | Example 18 (wt. %) | Example 19 (wt. %) |
|---|---|---|---|---|---|
| Sucralose | 1.7 | 2 | 2 | 1.5 | 0.5 |
| Neotame | 1 | 2 | 0 | | |
| Acesulfame potassium | 0.5 | 0.5 | 1 | 0.5 | |
| Rebaten 97% | 2 | 2 | 2 | 2 | 0.5 |
| Citric acid | 0.2 | 0.2 | 0.2 | 0.6 | 0.6 |
| Hydroxypropyl starch | 2 | 2 | 2 | 3 | 2 |
| Span20 | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Pigment | 0.1 | 0.1 | 0.1 | 0.1 | 0.1 |
| Polysorbate 80 | 0.4 | 0.5 | 0.3 | 0.3 | 0.3 |
| Peppermint oil | 0.8 | 2.7 | 0.6 | 3 | 3 |

TABLE 10-continued

| Ingredient | Example 15 (wt. %) | Example 16 (wt. %) | Example 17 (wt. %) | Example 18 (wt. %) | Example 19 (wt. %) |
|---|---|---|---|---|---|
| Pullulan | 62.3 | 77.5 | 55.1 | 81.5 | 78.9 |
| Microcrystalline cellulose | 1.4 | 1.4 | 0.7 | 1.5 | 4 |
| Beta cyclodextrin | | | 0.7 | | |
| Lemon flavor | 2 | 2 | 0.8 | 1.5 | 1.5 |
| Sildenafil free base | 25 | | | | |
| Sildenafil lactate | | 4.2 | | | |
| Sildenafil citrate | | | 35 | | |
| Granisetron hydrochloride | | | | 1 | |
| Montelukast sodium | | | | | 5 |
| Total weight | 100.0 | 100.0 | 100.0 | 100.0 | 100.0 |

Example 21

Sildenafil citrate based quickly soluble film prepared according to Example 18 of the present invention was subjected to pharmacokinetic tests in comparison with a conventional product named Viagra® tablet containing sildenafil citrate available from Pfizer Inc. The experiments is conducted for healthy eight (8) adult men and women with Latin square method based on Notice of bioequivalence test standard of the Food and Drug Administration.

The experimental results are shown in Table 11 and FIG. 3. It was confirmed that the inventive film of this example has the bioequivalence as shown in Table 11 and FIG. 3.

TABLE 11

Pharmacokinetic test result of sildenafil citrate film formulations

| Parameter | Group 1 | Group 2 |
|---|---|---|
| AUC0~24 (ng · hr/mL) | 711.87 ± 89.38 | 728.64 ± 87.10 |
| Cmax (ng/mL) | 255.39 ± 31.17 | 269.24 ± 88.90 |
| Tmax (hr) | 0.83 ± 0.42 | 0.81 ± 0.35 |

Note 1)
Group 1 is Bexcore sildenafil film formulations (25 mg).
Group 2 is Viagra ® tablets (25 mg)

Example 22

Using the Montelukast based quickly soluble film prepared in mixed ratio according to Example 20, as well as a commercially available solid dosage form, that is, Singulair® purchased by Merck & Co., as a control formulation, respectively, oral administration to Beagle dog was conducted to compare bioavailability of the foregoing materials.

More particularly, each test specimen was given to six (6) healthy male Beagle dogs, weighing 10.20 to 12.20 kg (10.99±0.87 kg), and these animals were subjected to basal breeding in separate cages for two (2) weeks before experiments. The control formulation administered to Beagle dogs was Singulair® chewable tablet (5 mg, Merck & Co.), while the inventive test formulation used therein was the formulation prepared in Example 20, which is a quickly soluble film containing 5 mg of Montelukast relative to 100 mg of the formulation. Beagle dogs were divided into two groups, each consisting of six (6) animals, and both groups received oral administration of the foregoing control formulation and test formulation, respectively. According to any conventional method for oral drug administration, 5 mg of the formulation was orally administered with water by force-feeding to each Beagle dog.

The experimental results are shown in Table 12 and FIG. 4. It was confirmed that the inventive film of this example has the bioequivalence as shown in Table 12 and FIG. 4.

TABLE 12

Pharmacokinetic test result of montelukast film formulations

| Parameter | Group 1 | Group 2 |
|---|---|---|
| AUC0~24 (ng · hr/mL) | 12398 ± 3029.7 | 12151.2 ± 1353.3 |
| Cmax (ng/mL) | 1010.7 ± 226.7 | 962.0 ± 73.2 |
| Tmax (hr) | 5.3 ± 3.3 | 4.0 ± 0.0 |

Note 1)
Group 1 is Bexcore montelukast based quickly soluble film formulations (5 mg).
Group 2 is Singulair ® chewable tablets (5 mg)

Example 23 to 27

As active pharmaceutical ingredients, Galantamine HBr, Doxazosin mesylate, Tolterodine tartrate, paroxetine hydrochloride and bambuterol hydrochloride were added to prepare films having constitutional compositions shown in the following Table 13. The sensory test was randomly conducted and test results were that unpleasant aftertaste was well masked.

TABLE 13

| Ingredient | Example 23 (wt. %) | Example 24 (wt. %) | Example 25 (wt. %) | Example 26 (wt. %) | Example 27 (wt. %) |
|---|---|---|---|---|---|
| Sucralose | 1.6 | 1.7 | 2 | 1.5 | |
| Aspartame | | | | | 2.5 |
| Acesulfame potassium | 0.6 | 0.5 | 0.7 | 0.5 | |
| Rebaten 97% | 2 | 1.9 | 2 | 2 | 1.5 |
| Citric acid | 0.2 | 0.2 | 0.2 | 0.6 | 0.6 |
| Hydroxypropyl starch | 2 | 2 | 2 | 3 | 2 |
| Span20 | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Pigment | 0.1 | 0.1 | 0.1 | 0.1 | 0.1 |
| Polysorbate 80 | 0.4 | 0.5 | 0.3 | 0.3 | 0.3 |
| Peppermint oil | 0.8 | 2.7 | 0.6 | 3 | 3 |
| Pullulan | 78.3 | 74.1 | 87.4 | 63.5 | 71.9 |
| Microcrystalline cellulose | 1.4 | 1.4 | 0.7 | 0.5 | 3 |
| Lemon flavor | 2 | 2 | 1.5 | 1.5 | 1.5 |
| Galantamine HBr | 10 | | | | |
| Doxazosin mesylate | | 10 | | | |
| Tolterodine tartrate | | | 2 | | |
| Paroxetine hydrochloride | | | | 20 | |
| Bambuterol hydrochloride | | | | | 10 |
| Total weight | 100.0 | 100.0 | 100.0 | 100.0 | 100.0 |

Example 28 to 32

As active pharmaceutical ingredients, pholcodine, butylscopolamine, fentanyl citrate, oxycodone HCl and buprenorphine HCl were added to prepare films having constitutional compositions shown in the following Table 14. The sensory test was randomly conducted and test results were that unpleasant aftertaste was well masked.

TABLE 14

| Ingredient | Example 28 (wt. %) | Example 29 (wt. %) | Example 30 (wt. %) | Example 31 (wt. %) | Example 32 (wt. %) |
|---|---|---|---|---|---|
| Sucralose | 1.7 | 1.5 | 2 | 1.5 | |
| Aspartame | | | | | 1.5 |
| Acesulfame potassium | 0.5 | 0.6 | 0.7 | 0.5 | |
| Rebaten 97% | 2 | 2 | 2 | 2 | 1.5 |
| Citric acid | 0.2 | 0.2 | 0.2 | 0.6 | 0.6 |
| Hydroxypropyl starch | 2 | 2 | 3.8 | 3 | 7 |
| Span20 | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Pigment | 0.1 | 0.1 | 0.1 | 0.1 | 0.1 |
| Polysorbate 80 | 0.4 | 0.5 | 0.3 | 0.3 | 0.3 |
| Peppermint oil | 0.8 | 2.7 | 1.6 | 3 | 3 |
| Pullulan | 78.3 | 74.1 | 86.4 | 71.5 | 74.9 |
| Microcrystalline cellulose | 1 | 1 | 0.4 | 0.5 | 3.5 |
| Beta cyclodextrin | 0.4 | 0.4 | 0.3 | 0.5 | 3.5 |
| Lemon flavor | 2 | 2 | 1.5 | 1 | 1.5 |
| Pholcodine | 10 | | | | |
| Butylscopolamine | | 10 | | | |
| Fentanyl citrate | | | 0.2 | | |
| Buprenorphine HCl | | | | 12 | |
| Oxycodone HCl | | | | | 5 |
| Total weight | 100.0 | 100.0 | 100.0 | 100.0 | 100.0 |

Example 33 to 37

As active pharmaceutical ingredients, hydromorphone HCl, escitalopram oxalate, rivastigmine tartrate, esomeprazole magnesium, and aripiprazole were added to prepare films having constitutional compositions shown in the following Table 15. The sensory test was randomly conducted and test results were that unpleasant aftertaste was well masked.

TABLE 15

| Ingredient | Example 33 (wt. %) | Example 34 (wt. %) | Example 35 (wt. %) | Example 36 (wt. %) | Example 37 (wt. %) |
|---|---|---|---|---|---|
| Sucralose | 1.7 | 1.6 | 2 | 1.5 | |
| Aspartame | | | | | 1.5 |
| Acesulfame potassium | 0.5 | 0.5 | 0.7 | 0.5 | |
| Rebaten 97% | 2 | 2 | 2 | 2 | 1.5 |
| Citric acid | 0.2 | 0.2 | 0.2 | 0.6 | 0.6 |
| Hydroxypropyl starch | 4 | 2 | 3.8 | 3 | 4 |
| Span20 | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Pigment | 0.1 | 0.1 | 0.1 | 0.1 | 0.1 |
| Polysorbate 80 | 0.4 | 0.5 | 0.3 | 0.3 | 0.3 |
| Peppermint oil | 0.8 | 2.7 | 0.6 | 3 | 3 |
| Pullulan | 79.3 | 74.1 | 81.6 | 71.5 | 61.9 |
| Microcrystalline cellulose | 4.4 | 1.4 | 3.7 | 2.5 | 2 |
| Lemon flavor | 2 | 2 | 1.5 | 1.5 | 1.5 |
| hydromorphone Hcl | 4 | | | | |
| Escitalopram oxalate | | 10 | | | |
| Rivastigmine tartrate | | | 3 | | |
| Aripiprazole | | | | 10 | |
| Esomeprazole magnesium | | | | | 20 |
| Total weight | 100.0 | 100.0 | 100.0 | 100.0 | 100.0 |

Example 38 to 42

As active pharmaceutical ingredients, zolmitriptan, rizatriptan benzoate, telmisartan, risperidone and vardenafil HCl were added to prepare films having constitutional compositions shown in the following Table 16. The sensory test was randomly conducted and test results were that unpleasant aftertaste was well masked.

TABLE 16

| Ingredient | Example 38 (wt. %) | Example 39 (wt. %) | Example 40 (wt. %) | Example 41 (wt. %) | Example 42 (wt. %) |
|---|---|---|---|---|---|
| Sucralose | 1.7 | 1.6 | 1 | 1.5 | |
| Neotame | | | 1 | | 1.5 |
| Acesulfame potassium | 0.5 | 0.5 | 0.7 | 0.5 | |
| Rebaten 97% | 2 | 2 | 2 | 2 | 1.5 |
| Citric acid | 0.2 | 0.2 | 0.2 | 0.6 | 0.6 |
| Hydroxypropyl starch | 3 | 2 | 2.8 | 3 | 4 |
| Span20 | 0.1 | 0.5 | 0.1 | 0.4 | 0.4 |
| Menthol | 0.4 | 2.3 | 0.3 | 3 | 3 |
| Carageenan | 0.1 | 0.1 | 0.1 | 0.1 | 0.2 |
| Pigment | 0.1 | 0.1 | 0.1 | 0.1 | 0.1 |
| Polysorbate 80 | 0.4 | 0.5 | 0.3 | 0.3 | 0.3 |
| Peppermint oil | 0.8 | 2.7 | 0.6 | 3 | 3 |
| Pullulan | 79.3 | 74.1 | 68.6 | 79.5 | 79.4 |
| Microcrystalline cellulose | 6.9 | 1.4 | 0.7 | 3.5 | 2 |
| Lemon flavor | 2 | 2 | 1.5 | 1.5 | 1.5 |
| Zolmitriptan | 2.5 | | | | |
| Rizatriptan benzoate | | 10 | | | |
| Telmisartan | | | 20 | | |
| Risperidone | | | | 1 | |
| Vardenafil HCl | | | | | 2.5 |
| Total weight | 100.0 | 100.0 | 100.0 | 100.0 | 100.0 |

Example 43 to 48

As active pharmaceutical ingredients, benzocain, loratidine, phenylephrine HCl, diphenhydramine HCl, Dextromethorphan hydrobromide, and cetrizine HCl were added to prepare films having constitutional compositions shown in the following Table 17. The sensory test was randomly conducted and test results were that unpleasant aftertaste was well masked.

TABLE 17

| Ingredient | Example 43 (wt. %) | Example 44 (wt. %) | Example 45 (wt. %) | Example 46 (wt. %) | Example 47 (wt. %) | Example 48 (wt. %) |
|---|---|---|---|---|---|---|
| Sucralose | 1.7 | 1.6 | 1 | 1.5 | 1 | 1 |
| Neotame | | | | | 0.5 | 0.5 |
| Acesulfame potassium | 0.5 | 0.5 | 0.7 | 0.5 | | |
| Rebaten 97% | 2 | 2 | 2 | 2 | 1.5 | 1.5 |
| Citric acid | 0.2 | 0.2 | 0.2 | 0.6 | 0.6 | 0.6 |
| Hydroxypropyl starch | 5 | 2 | 5 | 3 | 4 | 4 |
| Span20 | 0.1 | 0.5 | 0.1 | 0.4 | 0.4 | 0.4 |
| Menthol | 0.4 | 1.3 | 0.3 | 3 | 3 | 3 |
| Carageenan | 0.1 | 0.1 | 0.1 | 0.1 | 0.2 | 0.2 |
| Pigment | 0.1 | 0.1 | 0.1 | 0.1 | 0.1 | |
| Polysorbate 80 | 0.4 | 0.5 | 0.3 | 0.3 | 0.3 | 0.3 |
| Peppermint oil | 0.8 | 2.7 | 0.6 | 3 | 3 | 3 |
| Pullulan | 79.3 | 75.1 | 78.6 | 79.5 | 79.4 | 72 |
| Microcrystalline cellulose | 4.4 | 1.4 | 4.5 | 2 | 2 | 2 |
| Lemon flavor | 2 | 2 | 1.5 | 1.5 | 1.5 | 1.5 |
| Benzocain | 3 | | | | | |
| Loratadine | | 10 | | | | |
| Phenylephrine HCl | | | 5 | | | |
| Diphenhydramine HCl | | | | 2.5 | | |
| Dextromethorphan hydrobromide | | | | | 2.5 | |
| Cetrizine HCl | | | | | | 10 |
| Total weight | 100.0 | 100.0 | 100.0 | 100.0 | 100.0 | 100.0 |

In terms of dose acceptability, the inventive oral film dosage exhibited more excellent effects of masking a nasty taste. As is apparent from the foregoing description, the quickly soluble oral film dosage according to the present invention has advantages of efficiently masking a nasty taste, and being easily produced by simple processes at low cost. Therefore, the inventive oral film dosage may be effectively used in various applications such as an oral cleanser, a bad breath remover, a carrier for nutrient supplementary agent, and a tongue soluble formulation enabling absorption of drugs in the oral cavity as well as the stomach and bowels, and so forth.

While the present invention has been described with reference to exemplary embodiments, it will be understood by those skilled in the art that various modifications and variations may be made therein without departing from the scope of the present invention as defined by the appended claims.

What is claimed is:

1. A soluble oral film dosage, comprising:
   at least one water-soluble polymer; at least one active pharmaceutical ingredient; an aftertaste enhancer comprising a stevioside based sweetener which achieves peak sweetness in greater than 100 seconds; and at least one taste masking agent comprising a primary sweetening agent which achieves peak sweetness in less than 100 seconds;
   wherein the soluble oral film dosage contains 0.1 to 10 wt. % of the stevioside based sweetener;
   wherein the stevioside based sweetener and the primary sweetening agent are in a relative ratio by weight (w/w) of 1:3 to 3:1;
   wherein the primary sweetening agent is acesulfame-potassium, aspartame, or a mixture thereof, wherein a bitter and/or nasty taste is masked after one minute of dissolving the film in an oral cavity.

2. The soluble oral film dosage according to claim 1, wherein the soluble oral film dosage contains 0.1 to 10 wt. % of the primary sweetening agent.

3. The soluble oral film dosage according to claim 1, wherein the primary sweetening agent is acesulfame-potassium.

4. The soluble oral film dosage according to claim 1, wherein the primary sweetening agent is aspartame.

5. The soluble oral film dosage according to claim 1, wherein the stevioside based sweetener is stevioside.

6. The soluble oral film dosage according to claim 1, wherein the soluble oral film dosage contains 1.2 to 10 wt. % of the stevioside based sweetener.

7. A soluble oral film dosage, comprising:
   at least one water-soluble polymer;
   at least one active pharmaceutical ingredient;
   an aftertaste enhancer comprising a stevioside based sweetener; and
   at least one taste masking agent comprising a primary sweetening agent;
   wherein the primary sweetening agent is acesulfame-potassium, aspartame, or a mixture thereof;
   wherein the soluble oral film dosage contains 0.1 to 10 wt. % of the stevioside based sweetener; and
   wherein the stevioside based sweetener and the primary sweetening agent are in a relative ratio by weight (w/w) of 1:3 to 3:1, wherein a bitter and/or nasty taste is masked after one minute of dissolving the film in an oral cavity.

8. The soluble oral film dosage according to claim 7, wherein the stevioside based sweetener is at least one sweetener selected from the group consisting of stevioside, enzyme treated stevia and rebaudioside A.

9. The soluble oral film dosage according to claim 7, wherein the water-soluble polymer is at least one polymer selected from the group consisting of pullulan, gelatin, pectin, low viscosity pectin, hydroxypropylmethyl cellulose, low viscosity hydroxylpropylmethyl cellulose, hydroxyethyl cellulose, hydroxypropyl cellulose, carboxymethyl cellulose, polyvinylalcohol, polyacrylic acid, methyl methacrylate copolymer, carboxyvinyl polymer, polyethyleneglycol, alginic acid, low viscosity alginic acid, sodium alginate, modified starch, casein, whey protein extract, soy protein extract, zein, levan, elsinan, gluten, acacia gum, carageenan, Arabic gum, guar gum, locust bean gum, xanthan gum, gellan gum and agar.

10. The soluble oral film dosage according to claim 9, wherein the water-soluble polymer is at least one polymer selected from the group consisting of pullulan, gelatin, low viscosity pectin, low viscosity alginic acid and low viscosity hydroxylpropylmethyl cellulose.

11. The soluble oral film dosage according to claim 7, wherein the active pharmaceutical ingredient is at least one ingredient selected from the group consisting of diabetic remedy; insomnia remedy; genito-urinary remedy; obesity remedy; enzyme; gastric ulcer remedy; cough remedy and expectorant; dermal disorder remedy; antinausea drug; antidepression drug; antihistamine drug; antipyretic, analgesic and antiinflammatory drug; hormone drug; circulatory organ remedy; gastrointestinal remedy; psychoneurotic drug; impotency remedy; osteoporosis remedy; arthritis remedy; epilepsy remedy; muscle relaxing agent; cerebral function enhancer; schizophrenia remedy; immuno-suppression agent; antibiotic agent; anticancer agent; Supportives in tumor therapy; vaccine; oral cleanser; anemia remedy; constipation remedy; vitamin; nutrient; probiotic preparation; multi-symptom cold/influenza medications; and health functional foods.

12. The soluble oral film dosage according to claim 7, wherein the active pharmaceutical ingredient is at least one ingredient selected from the group consisting of triclosan, cetylpyridium chloride, domiphen bromide, quaternary ammonium salt, zinc compounds, sanguinarine, fluoride, alexidine, octenidine, EDTA, aspirin, acetaminophen, ibuprofen, ketoprofen, diflunisal, fenoprofen calcium, naproxen, tolmetin sodium, indomethacin, benzonatate, caramiphen, edisylate, menthol, dextromethorphan hydrobromide, chlophedianol hydrochloride, diphenhydramine, pseudoephedrine hydrochloride, phenylephrine, phenylpropanolamine, pseudoephedrine sulfate, bromophenylamine maleate, chlorophenylamine maleate, carbinoxamine maleate, clemastine fumarate, dexchlorpheniramine maleate, diphenhydramine hydrochloride, diphenhydramine citrate, diphenylpyraline hydrochloride, doxylamine succinate, promethazine hydrochloride, pyrilamine maleate, tripelennamine citrate, triprolidine hydrochloride, acrivastine, loratadine, brompheniramine, dexbrompheniramine, guaifenesin, ipecac, calcium iodide, terpine hydrate, loperamide, famotidine, ranitidine, omeprazole, lansoprazole, aliphatic alcohol, nicotine, caffeine, strychnine, picrotoxin, pentylenetetrazol, phenylhydantoin, phenobarbital, primidone, carbamazepine, ethosuximide, methosuximide, phensuximide, trimethadione, diazepam, benzodiazepine, phenacemide, pheneturide, acetazolamide and sulthiame, bromide levodopa, amantadine, morphine, heroin, hydromorphone, methophone, oxymorphone, levorphanol, codeine, hydrocodone, xycodone, nalorphine, naloxone, naltrexone, salicylate, phenylbutazone, indomethacin, phenacetin, chloropromazine, methotrimeprazine, haloperidol, clozapine, reserpine, imipramine, tranylcypromine, phenelzine, lithium, apomorphine, sildenafil, tadalafil, vardenafil, ondansetron, donepezil, zolpidem tartrate, granisetron, montelukast, pholcodine, butylscopolamine, fentanyl citrate, oxycodone hydrochloride, buprenorphine hydrochloride, escitalopram oxalate, rivastigmine tartrate, esomeprazole magnesium, aripiprazole, zolmitriptan, rizatriptan benzoate, telmisartan, risperidone, benzocaine, cetirizine hydrochloride, bambuterol hydrochloride, galantamine hydrobromide, lercanidipine hydrochloride, paroxetine hydrochloride, meloxicam, tolterodine tartrate, doxazosin mesylate, and pharmaceutically available salts thereof.

13. The soluble oral film dosage according to claim 7, wherein the soluble oral film dosage further comprises at least one additive.

14. The soluble oral film dosage according to claim 13, wherein the additive comprises at least one selected from the group consisting of a filler, a plasticizer, a secondary sweetening agent, an acidic agent, a flavor, an emulsifier, a pigment, and a cooling agent.

15. The soluble oral film dosage according to claim 14, wherein the filler is at least one selected from the group consisting of microcrystalline cellulose, cellulose polymer, magnesium carbonate, calcium carbonate, limestone powder, silicate, clay, talc, titanium dioxide and calcium phosphate.

16. The soluble oral film dosage according to claim 14, wherein the plasticizer is at least one selected from the group consisting of sorbitol, maltitol, xylitol, glycerin, polyethyleneglycol, propyleneglycol, hydrogenated starch syrup, starch syrup, triacetin, glycerol oleate, sucrose fatty acid ester and double chain fatty acid.

17. The soluble oral film dosage according to claim 14, wherein the secondary sweetening agent is at least one selected from the group consisting of sugar, glucose, maltose, oligosaccharides dextrin, alpha cyclodextrin, beta cyclodextrin, gamma cyclodextrin, hydroxypropyl beta cyclodextrin, methyl beta cyclodextrin, cluster dextrin, indigestible dextrin, hydrogenated indigestible dextrin, invert sugar, fructose, lactose, galactose, starch syrup, sorbitol, maltitol, xylitol, erythritol, hydrogenated starch syrup, mannitol and trehalose.

18. The soluble oral film dosage according to claim 14, wherein the acidic agent is at least one selected from the group consisting of citric acid, malic acid, fumaric acid, tartaric acid, ascorbic acid, succinic acid, adipic acid and lactic acid.

19. The soluble oral film dosage according to claim 14, wherein the flavor is a natural flavor, an artificial flavor or a mixture thereof.

20. The soluble oral film dosage according to claim 14, wherein the emulsifier is at least one selected from the group consisting of glycerin fatty acid ester, sucrose fatty acid ester, lecithin, enzyme treated lecithin, polysorbate, sorbitan fatty acid ester and propyleneglycol.

21. The soluble oral film dosage according to claim 7, wherein said at least one active pharmaceutical ingredient is ondansetron hydrochloride.

22. The soluble oral film dosage according to claim 7, wherein said at least one active pharmaceutical ingredient is montelukast sodium.

23. The soluble oral film dosage according to claim 7, wherein said at least one active pharmaceutical ingredient is sildenafil citrate.

24. The soluble oral film dosage according to claim 7, wherein said at least one active pharmaceutical ingredient is ondansetron hydrochloride; and
   wherein said soluble oral film dosage is bioequivalent to a commercially available tablet containing ondansetron hydrochloride.

25. The soluble oral film dosage according to claim 7, wherein said at least one active pharmaceutical ingredient is montelukast sodium; and
   wherein said soluble oral film dosage is bioequivalent to a commercially available chewable tablet containing montelukast sodium.

26. The soluble oral film dosage according to claim 7, wherein said at least one active pharmaceutical ingredient is sildenafil citrate; and
   wherein said soluble oral film dosage is bioequivalent to a commercially available tablet containing sildenafil citrate.

27. A soluble oral film dosage, comprising:
   at least one water-soluble polymer;
   at least one active pharmaceutical ingredient;
   an aftertaste enhancer comprising a stevioside based sweetener; and
   at least one taste masking agent comprising a primary sweetening agent;
   wherein the primary sweetening agent is selected from the group consisting of neotame, sucralose, acesulfame-potassium, aspartame, licorice extract, monellin, or a mixture thereof;
   wherein the soluble oral film dosage contains 0.1 to 10 wt. % of the stevioside based sweetener; and
   wherein the stevioside based sweetener and the primary sweetening agent are in a relative ratio by weight (w/w)

of 1:3 to 3:1, wherein a bitter and/or nasty taste is masked after one minute of dissolving the film in an oral cavity.

\* \* \* \* \*